United States Patent
Pittman et al.

(10) Patent No.: US 9,833,583 B2
(45) Date of Patent: Dec. 5, 2017

(54) SYSTEM AND METHOD FOR ADJUSTING TIDAL VOLUME OF A SELF-VENTILATION SUBJECT

(75) Inventors: Stephen Dalton Pittman, Brookline, MA (US); Erik Kurt Witt, Murrysville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 856 days.

(21) Appl. No.: 13/256,295

(22) PCT Filed: Feb. 22, 2010

(86) PCT No.: PCT/IB2010/050770
§ 371 (c)(1),
(2), (4) Date: Sep. 13, 2011

(87) PCT Pub. No.: WO2010/106451
PCT Pub. Date: Sep. 23, 2010

(65) Prior Publication Data
US 2012/0003620 A1    Jan. 5, 2012

Related U.S. Application Data

(60) Provisional application No. 61/161,881, filed on Mar. 20, 2009.

(51) Int. Cl.
*A61M 16/00* (2006.01)
*A63B 23/18* (2006.01)
(Continued)

(52) U.S. Cl.
CPC .......... *A61M 16/00* (2013.01); *A61M 16/161* (2014.02); *A63B 23/0244* (2013.01);
(Continued)

(58) Field of Classification Search
CPC ...... A61M 16/00; A61M 16/04; A61M 16/06; A61M 16/161; A63B 23/18; A63B 23/185; A63B 2024/0068; A63B 2230/40
(Continued)

(56) References Cited

U.S. PATENT DOCUMENTS 3,991,304 A    11/1976  Hillsman
4,495,944 A    1/1985   Brisson et al.
(Continued)

FOREIGN PATENT DOCUMENTS

EP    0667168    8/1995
GB    2307641    6/1997
(Continued)

OTHER PUBLICATIONS

Schein et al, "Treating Hypertension With a Device That Slows and Regularises Breathing: A Randomised, Double-Blind Controlled Study", Journal of Human Hypertension, vol. 15, No. 4, 2001, pp. 271-278.

(Continued)

*Primary Examiner* — Justine Yu
*Assistant Examiner* — Timothy Stanis

(57) ABSTRACT

A system and method are configured to adjust the tidal volume of the breathing of a subject. The subject is self-ventilating (breathes under her own power). The adjustment of tidal volume accomplished through use of the system and/or method may reduce hypertension (e.g., lower blood pressure), reduce stress and/or anxiety (and related maladies), improve relaxation, decrease sleep latency, improve sleep quality, address other sleep disorders, and/or provide other health benefits. The system and method are effective in adjusting tidal volume while the subject is awake and/or asleep.

15 Claims, 3 Drawing Sheets

(51) Int. Cl.
*A63B 23/02* (2006.01)
*A61M 16/16* (2006.01)
*A61M 16/04* (2006.01)
*A61M 16/06* (2006.01)
*A61M 16/10* (2006.01)
*A63B 24/00* (2006.01)
*A63B 71/06* (2006.01)

(52) U.S. Cl.
CPC ......... *A63B 23/185* (2013.01); *A61M 16/04* (2013.01); *A61M 16/06* (2013.01); *A61M 2016/0021* (2013.01); *A61M 2016/0039* (2013.01); *A61M 2016/102* (2013.01); *A61M 2205/332* (2013.01); *A61M 2205/3368* (2013.01); *A61M 2205/3375* (2013.01); *A61M 2205/3584* (2013.01); *A61M 2205/3592* (2013.01); *A61M 2205/505* (2013.01); *A61M 2205/52* (2013.01); *A61M 2205/581* (2013.01); *A61M 2205/582* (2013.01); *A61M 2205/583* (2013.01); *A63B 23/18* (2013.01); *A63B 2024/0068* (2013.01); *A63B 2071/0625* (2013.01); *A63B 2071/0627* (2013.01); *A63B 2071/0655* (2013.01); *A63B 2225/15* (2013.01); *A63B 2225/50* (2013.01); *A63B 2230/40* (2013.01); *A63B 2230/42* (2013.01); *A63B 2230/43* (2013.01)

(58) Field of Classification Search
USPC ............... 128/204.23, 905; 600/538–542
See application file for complete search history.

(56) References Cited

U.S. PATENT DOCUMENTS

| | | | |
|---|---|---|---|
| 4,981,295 A * | 1/1991 | Belman et al. | 482/13 |
| 5,800,337 A | 9/1998 | Gavish | |
| 5,921,238 A * | 7/1999 | Bourdon | 128/204.23 |
| 6,105,575 A | 8/2000 | Estes et al. | |
| 6,305,372 B1 * | 10/2001 | Servidio | 128/204.21 |
| 6,436,053 B1 | 8/2002 | Knapp et al. | |
| 6,920,875 B1 * | 7/2005 | Hill et al. | 128/204.18 |
| 7,556,038 B2 | 7/2009 | Kirby et al. | |
| 2004/0122334 A1 * | 6/2004 | Yamashiro | 600/534 |
| 2005/0256421 A1 * | 11/2005 | Bryant | 600/538 |
| 2007/0199566 A1 | 8/2007 | Be'eri | |
| 2009/0229611 A1 * | 9/2009 | Martin et al. | 128/204.21 |

FOREIGN PATENT DOCUMENTS

| | | |
|---|---|---|
| WO | WO0119245 | 3/2001 |
| WO | WO2007085109 | 8/2007 |

OTHER PUBLICATIONS

Radaelli et al, "Effects of Slow, Controlled Breathing on Baroreceptor Control of Heart Rate and Blood Pressure in Healthy Men" Journal of Hypertension, vol. 22, No. 7, 2004, p. 1361-1370.
Elliott et al, "Graded Blood Pressure Reduction in Hypertensnive Outpatients Associated Wdith Use of a Device to Assist With Slow Breathing", The Journal of Clinical Hypertension, vol. 6, No. 10, Oct. 2004, pp. 553-559.
St. Croix et al, "Role of Respiratory Motor Output in Within-Breath Modulation of Muscle Sympathetic Nerve Activity in Humans", Circulation Research, vol. 85, 1999, pp. 457-469.

* cited by examiner

SYSTEM AND METHOD FOR ADJUSTING TIDAL VOLUME OF A SELF-VENTILATION SUBJECT

This patent application claims the priority benefit under 35 U.S.C. §119(e) of U.S. Provisional Application No. 61/161,881 filed on Mar. 20, 2009, the contents of which are herein incorporated by reference.

The invention relates to the provision of breathing cues to a self-ventilating subject to prompt the self-ventilating subject to breathe under her own power with an increased tidal volume.

Hypertension is a significant problem in nearly all western cultures and is an underlying cause for stroke and heart attack. Termed the "Silent Killer," hypertension affects approximately 1 in 4 Americans, and occurs with even higher prevalence in some European communities. Hypertension is also gaining recognition as a co-morbid factor in obstructed sleep apnea (OSA) patient populations, with recent studies indicating that as many as 80% of patients seeking treatment for OSA may unknowingly suffer from this disease.

Several conventional systems and methods exist for prompting a subject to alter respiration in a manner that will provide physiological benefits, such as lower blood pressure. However, these systems and methods are generally focused on adjusting the timing and/or duration of inhalation and/or exhalation of subjects, and not on gas parameters of the gas being inhaled and/or exhaled by the subjects.

For example, U.S. patent application Ser. No. 11/836,292 to Kirby et al. ("Kirby"), which is hereby incorporated into this disclosure in its entirety, discloses a system for modifying the timing and/or duration of inhalation and exhalation of a subject through breathing cues. The breathing cues in Kirby are provided to the subject in the form a pressurized flow of breathable gas delivered to the airway of the subject. U.S. Pat. No. 5,800,337 to Gavish ("Gavish"), which is hereby incorporated into this disclosure in its entirety, discloses another system of interest.

One aspect of the invention relates to a system configured to adjust the tidal volume of the breathing of a self-ventilating subject. In one embodiment, the system comprises a device configured to provide breathing cues to a self-ventilating subject that prompt the self-ventilating subject to breathe such that the tidal volume of the breathing of the self-ventilating subject is greater than or equal to a target tidal volume.

Another aspect of the invention relates to a method for adjusting the tidal volume of the breathing of a self-ventilating subject. In one embodiment, the method comprises providing breathing cues to a self-ventilating subject that prompt the self-ventilating subject to breathe such that the tidal volume of the breathing of the self-ventilating subject is greater than or equal to a target tidal volume.

Another aspect of the invention relates to a system configured to adjust the tidal volume of the breathing of a self-ventilating subject. In one embodiment, the system comprises means for providing breathing cues to a self-ventilating subject that prompt the self-ventilating subject to breathe such that the tidal volume of the breathing of the self-ventilating subject is greater than or equal to a target tidal volume.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
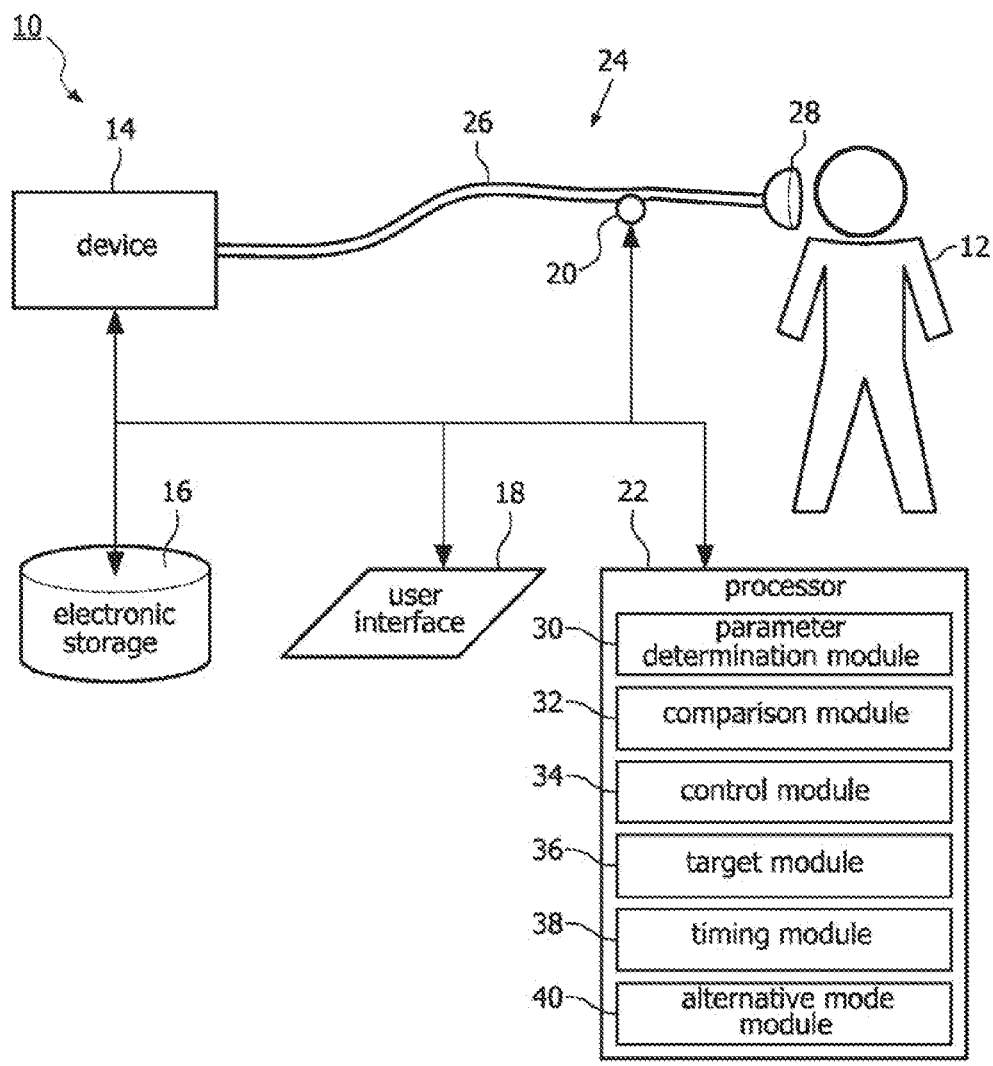
FIG. 1 illustrates a system configured to adjust the tidal volume of the breathing of a subject, in accordance with one or more embodiments of the invention.

FIG. 1 illustrates a system 10 configured to adjust the tidal volume of the breathing of a subject 12. Subject 12 is self-ventilating (breathes under her own power). The adjustment of tidal volume accomplished through use of system 10 may reduce hypertension (e.g., lower blood pressure), reduce stress and/or anxiety (and related maladies), improve relaxation, decrease sleep latency, improve sleep quality, address other sleep disorders, and/or provide other health benefits. System 10 is effective in adjusting tidal volume while subject 12 is awake and/or asleep. To adjust the tidal volume of the breathing of subject 12, system 10 may provide breathing cues to subject 12 that encourage subject 12 to maintain a tidal volume that is at or above a target tidal volume. In one embodiment, system 10 may include a device 14, electronic storage 16, a user interface 18, one or more sensors 20, a processor 22, and/or other components.

In one embodiment, device 14 includes a positive pressure support device. A positive pressure support device is well-known and is disclosed, for example, in U.S. Pat. No. 6,105,575, hereby incorporated by reference in its entirety. In this embodiment, device 14 is configured to deliver a pressurized flow of breathable gas to the airway of subject 12.

Device 14 may be configured to generate the pressurized flow of breathable gas according to one or more modes. A non-limiting example of one such mode is Continuous Positive Airway Pressure (CPAP). CPAP has been used for many years and has proven to be helpful in promoting regular breathing. Another mode for generating the pressurized flow of breathable gas is Inspiratory Positive Air Pressure (IPAP). One example of the IPAP mode is bi-level positive air pressure (BiPAP). In BiPAP, two levels of positive air pressure (HI and LO) are supplied to a patient. Other modes of generating the pressurized flow of breathable gas are contemplated.

Generally, the timing of the HI and LO levels of pressure are controlled such that the HI level of positive air pressure is delivered to subject 12 during inhalation and the LO level of pressure is delivered to subject 12 during exhalation. In conventional positive pressure support devices, the timing of the HI and LO levels of pressure is coordinated to coincide with the breathing of subject 12 based on detection of gas parameters that indicate whether a user is currently inhaling or exhaling.

As was mentioned above, device 14 may be configured to deliver breathing cues to subject 12 to influence the breathing of subject 12 to achieve a target tidal volume during breathing. In one embodiment, the breathing cues include changes to one or more parameters of the pressurized flow of breathable gas. This is not intended to be limiting, as in some embodiments, the breathing cues may include one or more of audible cues, visual cues, tactile cues, and/or sensory cues that provide breathing guidance to subject 12. In embodiments including audible cues, visual cues, and/or tactile cues, device 14 may not include a positive pressure support device that delivers a pressurized flow of breathable gas.

The pressurized flow of breathable gas is delivered to the airway of subject 12 via a subject interface 24. Subject interface 24 is configured to communicate the pressurized flow of breathable gas generated by device 14 to the airway of subject 12. As such, subject interface 24 includes a conduit 26 and an interface appliance 28. Conduit conveys the pressurized flow of breathable gas to interface appliance 28, and interface appliance 28 delivers the pressurized flow of breathable gas to the airway of subject 12. Some examples of interface appliance 28 may include, for example, an endotracheal tube, a nasal cannula, a tracheotomy tube, a nasal mask, a nasal/oral mask, a full face mask, a total face mask, or other interface appliances that communication a flow of gas with an airway of a subject. The present invention is not limited to these examples, and contemplates delivery of the pressurized flow of breathable gas to subject 12 using any subject interface.

In one embodiment, electronic storage 16 comprises electronic storage media that electronically stores information. The electronically storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 22, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., device 14, user interface 18, processor 22, etc.).

User interface 18 is configured to provide an interface between system 10 and subject 12 through which subject 12 may provide information to and receive information from system 10. This enables data, results, and/or instructions and any other communicable items, collectively referred to as "information," to be communicated between the subject 12 and one or more of device 14, electronic storage 16, and/or processor 22. Examples of interface devices suitable for inclusion in user interface 18 include a keypad, buttons, switches, a keyboard, knobs, levers, a display screen, a touch screen, speakers, a microphone, an indicator light, an audible alarm, a printer, and/or other interface devices. In one embodiment, user interface 18 includes a plurality of separate interfaces. In one embodiment, user interface 18 includes at least one interface that is provided integrally with device 14.

It is to be understood that other communication techniques, either hardwired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

One or more sensors 20 are configured to generate one or more output signals conveying information related to one or more gas parameters of the gas breathed by subject 12. The one or more parameters may include, for example, one or more of a flow rate, a volume, a pressure, a composition (e.g., concentration(s) of one or more constituents), humidity, temperature, acceleration, velocity, acoustics, changes in a parameter indicative of respiration, and/or other gas parameters. In an embodiment in which a pressurized flow of breathable gas is delivered to subject 12 from device 14, sensors 20 include sensors in communication with gas within subject interface 24.

Processor 22 is configured to provide information processing capabilities in system 10. As such, processor 22 may include one or more of a digital processor, an analog processor, a digital circuit designed to process information, an analog circuit designed to process information, a state machine, and/or other mechanisms for electronically processing information. Although processor 22 is shown in FIG. 1 as a single entity, this is for illustrative purposes only. In some implementations, processor 22 may include a plurality of processing units. These processing units may be physically located within the same device, or processor 22 may represent processing functionality of a plurality of devices operating in coordination. In one embodiment, the functionality attributed below to processor 22 is provided, at least in part, by processing components disposed within device 14.

As is shown in FIG. 1, in one embodiment, processor 22 includes a parameter determination module 30, a comparison module 32, a control module 34, a target module 36, a timing module 38, an alternative mode module 40 and/or other modules. Modules 30, 32, 34, 36, 38, and/or 40 may be implemented in software; hardware; firmware; some combination of software, hardware, and/or firmware; and/or otherwise implemented. It should be appreciated that although modules 30, 32, 34, 36, 38, and/or 40 are illustrated in FIG. 1 as being co-located within a single processing unit, in implementations in which processor 22 includes multiple processing units, modules 30, 32, 34, 36, 38, and/or 40 may be located remotely from the other modules. Further, the description of the functionality provided by the different modules 30, 32, 34, 36, 38, and/or 40 described below is for illustrative purposes, and is not intended to be limiting, as any of modules 30, 32, 34, 36, 38, and/or 40 may provide more or less functionality than is described. For example, one or more of modules 30, 32, 34, 36, 38, and/or 40 may be eliminated, and some or all of its functionality may be provided by other ones of modules 30, 32, 34, 36, 38, and/or 40. As another example, processor 22 may include one or more additional modules that may perform some or all of the functionality attributed below to one of modules 30, 32, 34, 36, 38, and/or 40.

Parameter determination module 30 is configured to determine a breathing parameter from the one or more output signals generated by sensors 20. The breathing parameter is either the tidal volume of the breathing of subject 12 or a gas parameter of the gas breathed by the subject 12 that is related to tidal volume. As such, the breathing parameter describes a parameter of the gas that is breathed by subject 12, and not just any breathing parameter generally. For example, timing parameters of inhalation and/or exhalation (e.g., duration, frequency, relative length, etc.) may be considered parameters of breathing generally, but would not constitute breathing parameters as determined by parameter determination module 30. Instead, the breathing parameter determined by parameter determination module 30 is limited to parameters of the actual gas breathed by subject 12 (e.g., flow rate, peak flow, tidal volume, pressure, composition, humidity, temperature, acceleration, velocity, acoustics, thermal energy dissipated (e.g., a mass flowmeter), changes in a parameter indicative of respiration, and/or other parameters related to the actual gas breathed by subject 12). If the breathing parameter is a parameter of individual breaths (e.g., tidal volume, peak flow, etc.), determining the breathing parameter may include aggregating the value of the breathing parameter over several breaths. For example, determined values of the breathing parameter over several breaths may be averaged.

Comparison module 32 is configured to compare the breathing parameter determined by parameter determination module 30 to a target threshold. If the breathing parameter is tidal volume, the target threshold is a target tidal volume. If the breathing parameter is a gas parameter related to tidal volume, the target threshold is a threshold that corresponds to the target tidal volume. The target tidal volume is the tidal volume at which system 10 is attempting to get subject 12 to breathe at.

Control module 34 is configured to control device 14. Controlling device 14 includes adjusting the breathing cues provided to subject 12 by device 14. As was mentioned above, in one embodiment, the breathing cues administered to subject 12 by device 14 include changes to one or more parameters of the pressurized flow of breathable gas delivered from device 14 to subject 12. For example, the one or more parameters may include a pressure, a flow rate, and/or a volume of the pressurized flow of breathable gas. Control module 34 adjusts the breathing cues provided to subject 12 be device 14 in order to prompt subject 12 to breathe with a tidal volume that is at or above the target tidal volume.

For example, in an embodiment in which device 14 generates the pressurized flow of breathable gas according to a BiPAP mode, control module 34 may control device 14 to adjust the pressure, flow rate, and/or volume of gas delivered to the airway of subject 12 while the pressurized flow of breathable gas is being generated at the HI pressure (e.g, during inhalation). Increasing the pressure, flow rate, and/or volume of gas delivered to the airway of subject 12 while the pressurized flow of breathable gas is being generated at the HI pressure will increase the volume of gas inhaled by subject 12, thereby increasing the tidal volume of respiration of subject 12. Similarly, decreasing the pressure, flow rate, and/or volume of gas delivered to the airway of subject 12 while the pressurized flow of breathable gas is being generated at the HI pressure will prompt subject 12 to decrease the tidal volume of respiration.

As another example, in an embodiment in which device 14 generates the pressurized flow of breathable gas according to a BiPAP mode, control module 34 may control device 14 to adjust the pressure flow rate, and/or volume of gas delivered to the airway of subject 12 while the pressurized flow of breathable gas is being generated at the LO pressure (e.g., during exhalation). Decreasing the pressure, flow rate, and/or volume of gas delivered to the airway of subject 12 while the pressurized flow of breathable gas is being generated at the LO pressure may increase the volume gas that is exhaled by subject 12, thereby increasing the tidal volume of respiration of subject 12. Increasing the pressure, flow rate, and/or volume of gas delivered to the airway of subject 12 while the pressurized flow of breathable gas is being generated at the LO pressure will prompt subject 12 to decrease the tidal volume of respiration.

Figure 2:
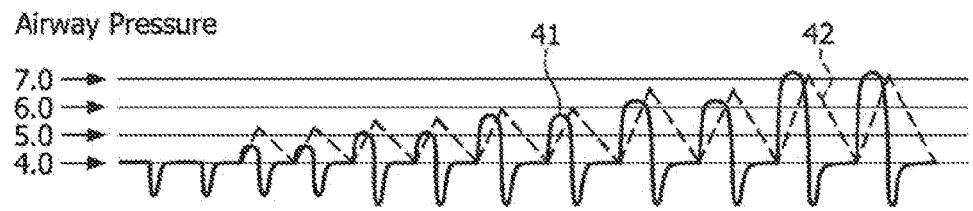
FIG. 2 illustrates a plot of pressure of a pressurized flow of breathable gas delivered to the airway of a subject and a plot of the tidal volume of the breathing of the subject receiving the pressurized flow of breathable gas, according to one or more embodiments of the invention.

By way of illustration, FIG. 2 illustrates a plot of pressure 41 of the pressurized flow of breathable gas and a plot of the tidal volume 42 of a subject receiving the pressurized flow of breathable gas (e.g., subject 12 illustrated in FIG. 1) on the same time axis. As can be seen in FIG. 2, as the pressure at which the pressurized flow of breathable gas is delivered to the subject is increased during the HI pressure periods, the tidal volume of the breaths tends to be increased by the user voluntarily through deeper breathing.

Returning to FIG. 1, in one embodiment, adjustments to the parameters of the pressurized flow of breathable gas made by control module 34 are made in a feedback manner. In this embodiment, adjustments to the parameters of the pressurized flow of breathable gas may be determined based on the comparison between the breathing parameter and the target threshold made by comparison module 32. For example, if comparison module 32 determines that the breathing parameter is below the target threshold (and/or has remained under the target threshold for a predetermined period of time), control module 34 may increase the pressure, flow rate, and/or volume of gas delivered to the airway of subject 12 while the pressurized flow of breathable gas is being generated at the HI pressure. If comparison module 32 determines that the breathing parameter is above the target threshold by a predetermined amount and/or for a predetermined period of time, control module 34 may reduce the pressure flow rate, and/or volume of gas delivered to the airway of subject 12 while the pressurized flow of breathable gas is being generated at the HI pressure. This may the additional effect of giving a cue to subject 12 to increase or decrease depth of breathing.

In one embodiment, adjustments to the parameters of the pressurized flow of breathable gas are not made in a feedback manner. In this embodiment, relationships between tidal volume and one or more parameters of the pressurized flow of breathable gas are determined in advance. These predetermined relationships are then used to generate the pressurized flow of breathable gas with parameters that correspond to the target tidal volume. In this embodiment, processor 22 may not include comparison module 32 and/or sensors 20.

Target module 36 is determined to obtain a target tidal volume. In one embodiment, the target tidal volume is received from a user (e.g., a caregiver, subject 12, etc.). The user may input the target tidal volume via user interface 18. Inputting the target tidal volume may include inputting a new target tidal volume, or adjusting a previously obtained target tidal volume.

In one embodiment, the target tidal volume is determined by target module 36 based on a determination of the typical tidal volume of subject 12. For example, the target tidal volume may be set at a predetermined amount above the typical tidal volume of subject 12. A determination of the typical tidal volume of subject 12 may be based on the breathing parameter determined by parameter determination module 30.

In one embodiment, target module 36 sets the target tidal volume at an initial level, and then slowly increases the target tidal volume over time. The initial level may be based on the baseline tidal volume of subject 12, and/or may be a preset value. The baseline tidal volume of subject 12 may be determined prior to a period of deeper respiration. The target tidal volume may be increased over time until it reaches a final target tidal volume. Increasing the target tidal volume over time may enhance the comfort of the breathing cues provided to subject 12. Increasing the target tidal volume over time may include incrementing the target tidal volume, increasing the target tidal volume over time smoothly, and/or otherwise increasing the target tidal volume.

In one embodiment, target module 36 adjusts the target tidal volume based on the breathing parameter determined by parameter determination module 30. For example, after target module 36 increases the target tidal volume, the breathing cues provided to subject 12 by device 14 will be adjusted by control module 34 to reflect the new target tidal volume. Target module 36 may then monitor the compliance of subject 12 with the new target tidal volume (e.g., based on comparisons made by comparison module 32). If it is determined that subject 12 is complying with the new target tidal volume, target module 36 will then continue to increase the target tidal volume toward the final target tidal volume. If it is determined that subject 12 is not complying with the new target tidal volume, then target module 36 will take a different action. For instance, target module 36 may maintain the target tidal volume at a constant level until subject 12 begins to comply, or target module 36 may reduce the target tidal volume until subject 12 is again in compliance before resuming the increase of the target tidal volume.

In one embodiment, the breathing parameter determined by parameter determination module 30 and used for comparison by comparison module 32 is a gas parameter other than tidal volume. In this embodiment, target module 36 controls and/or adjusts the target tidal volume by controlling or adjusting a target threshold for the breathing parameter that corresponds to the target tidal volume. As was mentioned above, this target threshold for the breathing parameter is then used by comparison module 32 to monitor compliance of subject 12 with the target tidal volume.

In one embodiment, timing module 38 is configured to determine an amount of time for which subject 12 has maintained her tidal volume at or above the target tidal volume. This amount of time signifies the amount of treatment that subject 12 has received from system 10. Timing module 38 determines the amount of time for which subject 12 has maintained an appropriate tidal volume from the one or more output signals generated by sensors 20. For example, timing module 38 may determine the amount of time for which subject 12 has maintained an appropriate tidal volume based on comparisons by comparison module 32. Determining the amount of time for which subject 12 has maintained an appropriate tidal volume may include adding separate, temporally non-adjacent periods of time during which subject 12 maintained the appropriate tidal volume.

In one embodiment, system 10 is configured to provide treatment to subject 12 for a predetermined amount of treatment that is quantified by an amount of time that the tidal volume of subject 12 is maintained at or above the target tidal volume. In this embodiment, once the predetermined amount of therapy has been reached (as determined by timing module 38), timing module 38 provides an output to subject 12 (e.g., via user interface 18) indicating that the predetermined amount of treatment has been reached.

In one embodiment, timing module 38 provides information related to the amount of treatment received by subject 12 to a user (e.g., a caregiver, the subject, etc.). For example, timing module 38 may output the information to the user via user interface 18. As another example, timing module 38 may store the information to electronic storage 16 for access by the user.

Alternative mode module 40 is configured to control device 14 in one or more modes other than the provision of breathing cues to subject 12 to increase tidal volume. For example, if device 14 is configured to generate a pressurized flow of breathable gas, alternative mode module 40 controls device 14 in one or more alternative pressure generation modes. The one or more alternative pressure generation modes may include, for example, one or more airway support modes, one or more sleep disordered breathing diagnostic modes, one or more ventilation modes, and/or other modes of pressure generation. In one embodiment, alternative mode module 40 is configured to assume control of device 14 once a predetermined amount of treatment has been achieved (as determined by timing module 38).

For instance, device 14 may be controlled initially by control module 34 to provide breathing cues to subject 12 that increase tidal volume, thereby increasing relaxation of subject 12. The relaxation experienced by subject 12 may induce sleepiness, or even sleep. Upon receiving a predetermined amount of treatment, subject 12 is asleep or ready for sleep, and alternative mode module 40 assumes control over device 14 so that the pressurized flow of breathable gas provides airway support to subject 12 during sleep.

Figure 3:
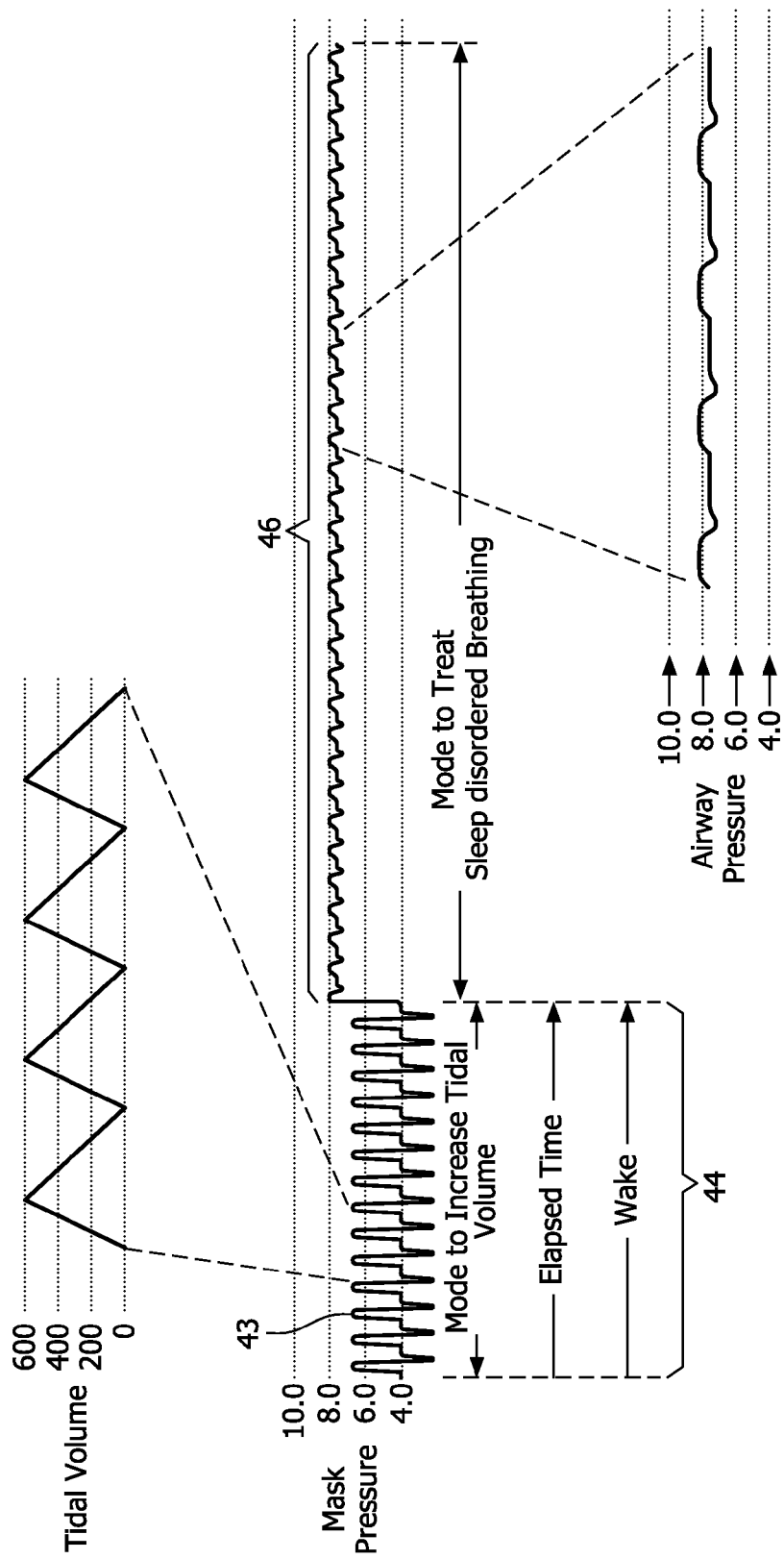
FIG. 3 illustrates a plot of pressure of a pressurized flow of breathable gas delivered to the airway of a subject and a plot of the tidal volume of the breathing of the subject receiving the pressurized flow of breathable gas, according to one or more embodiments of the invention.

By way of illustration, FIG. 3 shows a plot of pressure 43 at or near the airway of a subject (e.g., subject 12) over time. The plot illustrates how during a first period of time 44 the tidal volume of the subject is increased by manipulating the pressure, flow, and/or volume of the pressurized flow of breathable gas transmitted to the airway of the subject. The plot further illustrates how during a second period of time 46 the pressurized flow of breathable gas is delivered to the subject to provide airway support that overcomes sleep disordered breathing.

In one embodiment, transition of control over device 14 from control module 34 to alternative mode module 40 may be triggered by something other than a determination of the amount of therapy received. For example, processor 22 may determine from the output signals of sensors 20 whether subject 12 is asleep or awake, and may trigger a transition of control over device 14 from control module 34 to alternative mode module 40 when it is determined that subject 12 has fallen asleep.

Figure 4:
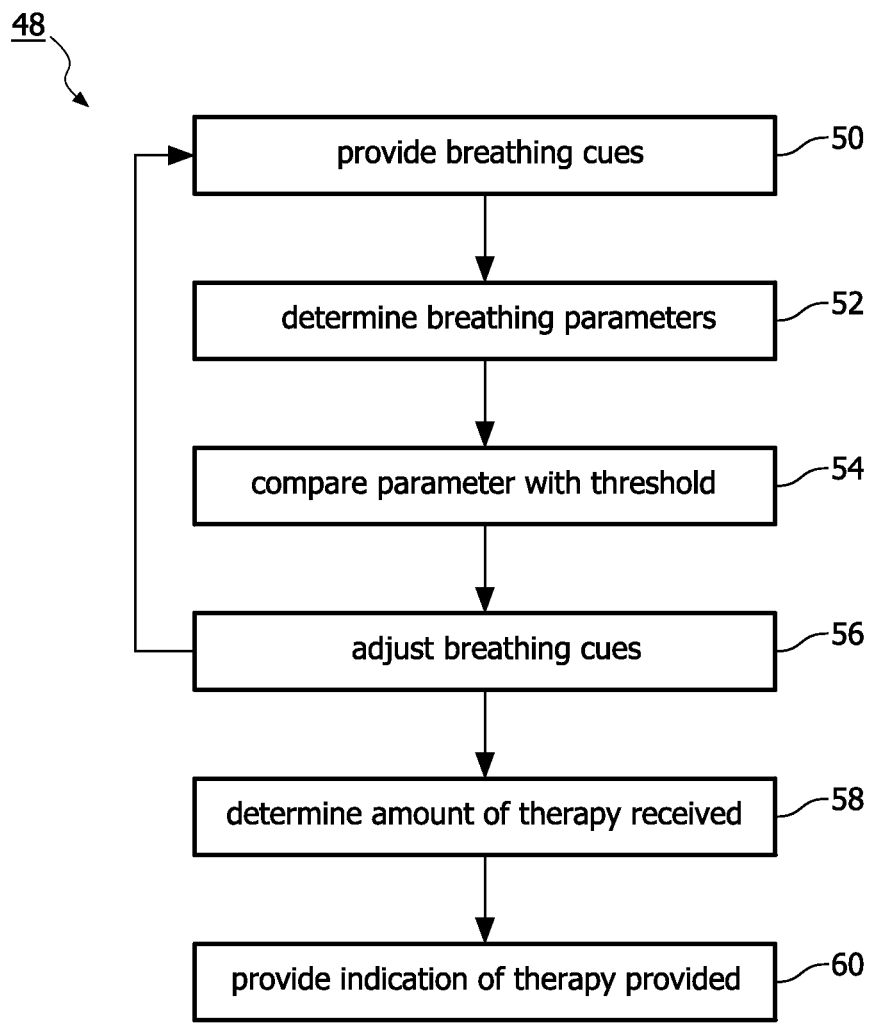
FIG. 4 illustrates a method for therapeutically controlling the tidal volume of the respiration of a subject, in accordance with one or more embodiments of the invention.

FIG. 4 illustrates a method 48 for therapeutically controlling the tidal volume of the respiration of a subject that is self-ventilating. The operations of method 48 presented below are intended to be illustrative. In some embodiments, method 48 may be accomplished with one or more additional operations not described, and/or without one or more of the operations discussed. Additionally, the order in which the operations of method 48 are illustrated in FIG. 4 and described below is not intended to be limiting. In some embodiments, method 48 may be implemented in a system that is similar to or the same as system 10 (shown in FIG. 1 and described above).

At an operation 50, breathing cues are provided to the self-ventilating subject. The breathing cues prompt the subject to breathe such that the tidal volume of the breathing of the subject is greater than or equal to a target tidal volume. In one embodiment, the breathing cues include changes in one or more parameters of a pressurized flow of breathable gas being delivered to the airway of the subject. In one embodiment, the breathing cues are provided by a device that is the same as or similar to device 14 (shown in FIG. 1 and described above). The device may be controlled by a control module that is the same as or similar to control module 34 (shown in FIG. 1 and described above).

At an operation 52, a breathing parameter of the subject is determined. The breathing parameter is either the tidal volume of the breathing of the subject or a gas parameter so the gas breathed by the subject that is related to the tidal volume. As such, the breathing parameter is not a timing and/or duration of inhalation and/or exhalation. In one embodiment, operation 52 is performed by a parameter determination module that is the same as or similar to parameter determination module 30 (shown in FIG. 1 and described above).

At an operation 54, the breathing parameter determined at operation 52 is compared with a target threshold. The target threshold is, or corresponds to, a target tidal volume. In one embodiment, operation 54 is performed by a comparison module that is the same as or similar to comparison module 32.

In one embodiment, the target threshold is adjusted over time so that the target tidal volume is increased over time. For example, adjustment of the target threshold may be performed by a target module that is the same as or similar to target module 36 (shown in FIG. 1 and described above).

At an operation 56, the breathing cues provided to the subject are adjusted. The adjustment to the breathing cues is determined based on the comparison performed at operation 54. In one embodiment, operation 56 is performed by a control module that is similar to or the same as control module 34 (shown in FIG. 1 and described above).

At an operation 58, an amount of therapy received by the subject is determined. The amount of therapy may include an amount of time at which the tidal volume of respiration of the subject has been maintained at or above a target tidal volume. The determination of the amount of therapy received by the subject may be determined based on the breathing parameter determined at operation 54 and/or the comparison of the breathing parameter to a target threshold at operation 56. In one embodiment, operation 56 is performed by a timing module that is the same as or similar to timing module 38 (shown in FIG. 1 and described above).

At an operation 60, an indication of the amount of therapy received by the subject is provided to a user (e.g., the subject, a caregiver, etc.). The indication of the amount of therapy received by the subject may include an audio and/or visual output, a change in one or more parameters of a pressurized flow of breathable gas being provided to the airway of the subject, storage of information related to the amount of therapy received by the subject, and/or other indications. In one embodiment, operation 60 is provided by a timing module that is the same as or similar to timing module 38 (shown in FIG. 1 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to adjust a tidal volume of the breathing of a self-ventilating subject, the system comprising:
    one or more sensors that generate output signals conveying information related to one or more gas parameters of gas breathed by the self-ventilating subject;
    a positive pressure support device configured to provide a pressurized flow of breathable gas to an airway of the self-ventilating subject; and
    a processor configured to execute one or more modules, the one or more modules comprising:
        a parameter determination module configured to determine a breathing parameter from the output signals generated by the one or more sensors, wherein the breathing parameter reflects a tidal volume of the gas breathed by the self-ventilating subject;
        a control module configured to control the positive pressure support device to provide breathing cues to the self-ventilating subject that prompt the self-ventilating subject to breathe voluntarily in a way such that the tidal volume of the gas breathed by the self-ventilating subject is greater than or equal to a current target tidal volume, wherein the breathing cues include changes in a pressure of the provided pressurized flow of breathable gas; and
        a target module configured to adjust the current target tidal volume over time up and down between an initial target tidal volume and a final target tidal volume, such adjustment being based on the breathing parameter determined by parameter determination module.

2. The system of claim 1, wherein the one or more modules further comprise:
    a comparison module configured to compare the breathing parameter to a threshold that corresponds to the target tidal volume,
    wherein the control module is configured to adjust the breathing cues provided to the self-ventilating subject based on the comparison between the breathing parameter and the threshold by the comparison module.

3. The system of claim 2, wherein the one or more modules further comprise a timing module configured to determine from the one or more output signals generated by the one or more sensors an amount of time for which the self-ventilating subject has maintained the breathing parameter above the threshold.

4. The system of claim 1, wherein the target module is configured such that adjustment of the current target tidal volume over time up and down between an initial target tidal volume and a final target tidal volume includes determining compliance of the self-ventilating subject with the current target tidal volume for a predetermined period of time, and responsive to such determination, incrementing or decreasing the current target tidal volume.

5. The system of claim 1, wherein the self-ventilating subject breathes under his own power, wherein the breathing cues do not provide the tidal volume of the breathing, and wherein the breathing cues do not substantially supplement respiratory effort of the subject.

6. A method for adjusting a tidal volume of the breathing of a self-ventilating subject, the method comprising:
providing a pressurized flow of breathable gas to an airway of the self-ventilating subject;
generating output signals conveying information related to one or more gas parameters of gas breathed by the self-ventilating subject;
determining a breathing parameter from the output signals, wherein the breathing parameter reflects a tidal volume of the gas breathed by the self-ventilating subject; and
providing breathing cues to the self-ventilating subject that prompt the self-ventilating subject to breathe voluntarily in a way such that the tidal volume of the gas breathed by the self-ventilating subject is greater than or equal to a current target tidal volume, wherein the breathing cues include changes in a pressure of the provided pressurized flow of breathable gas;
adjusting the current target tidal volume over time up and down between an initial target tidal volume and a final target tidal volume, such adjustment being based on the breathing parameter.

7. The method of claim 6, further comprising:
comparing the breathing parameter to a threshold that corresponds to the target tidal volume,
wherein providing breathing cues includes adjusting the breathing cues provided to the self-ventilating subject based on the comparison between the breathing parameter and the threshold.

8. The method of claim 7, further comprising determining an amount of time for which the self-ventilating subject has maintained the breathing parameter above the threshold.

9. The method of claim 6, further comprising determining compliance of the self-ventilating subject with the current target tidal volume for a predetermined period of time, and responsive to such determination, incrementing or decreasing the current target tidal volume.

10. The method of claim 6, wherein the self-ventilating subject breathes under his own power, wherein the breathing cues do not provide the tidal volume of the breathing, and wherein the breathing cues do not substantially supplement respiratory effort of the subject.

11. A system configured to adjust a tidal volume of the breathing of a self-ventilating subject, the system comprising:
means for providing a pressurized flow of breathable gas to an airway of the self-ventilating subject;
means for generating output signals conveying information related to one or more gas parameters of gas breathed by the self-ventilating subject;
means for determining a breathing parameter from the output signals, wherein the breathing parameter reflects a tidal volume of the gas breathed by the self-ventilating subject; and
means for providing breathing cues to the self-ventilating subject that prompt the self-ventilating subject to breathe voluntarily in a way such that the tidal volume of the gas breathed by the self-ventilating subject is greater than or equal to a current target tidal volume, wherein the breathing cues include changes in a pressure of the provided pressurized flow of breathable gas;
means for adjusting the current target tidal volume over time up and down between an initial target tidal volume and a final target tidal volume, such adjustment being based on the breathing parameter determined by the means for determining breathing parameter.

12. The system of claim 11, further comprising:
means for comparing the breathing parameter to a threshold that corresponds to the target tidal volume,
wherein the means for providing breathing cues includes a means for adjusting the breathing cues provided to the self-ventilating subject based on the comparison between the breathing parameter and the threshold.

13. The system of claim 12, further comprising means for determining an amount of time for which the self-ventilating subject has maintained the breathing parameter above the threshold.

14. The system of claim 11, further comprising means for determining compliance of the self-ventilating subject with the current target tidal volume for a predetermined period of time, wherein the means for determining compliance include means for incrementing or decreasing the current target tidal volume.

15. The system of claim 11, wherein the self-ventilating subject breathes under his own power, wherein the breathing cues do not provide the tidal volume of the breathing, and wherein the breathing cues do not substantially supplement respiratory effort of the subject.

* * * * *